(12) United States Patent
Lee

(10) Patent No.: US 7,320,687 B2
(45) Date of Patent: Jan. 22, 2008

(54) TENDON STRIPPER

(76) Inventor: Thomas H. Lee, 374 Jessing Trail, Columbus, OH (US) 43235

(*) Notice: Subject to any disclaimer, the term of this patent is extended or adjusted under 35 U.S.C. 154(b) by 274 days.

(21) Appl. No.: 11/121,747

(22) Filed: May 4, 2005

(65) Prior Publication Data

US 2006/0264993 A1    Nov. 23, 2006

(51) Int. Cl.
*A61B 17/56*    (2006.01)
(52) U.S. Cl. ...................................... 606/96
(58) Field of Classification Search ............... 623/13, 623/17; 606/37, 39, 45, 113
See application file for complete search history.

(56) References Cited

U.S. PATENT DOCUMENTS

| | | | |
|---|---|---|---|
| 4,773,417 A | 9/1988 | Moore et al. | |
| 5,139,520 A | 8/1992 | Rosenberg | |
| 5,522,827 A * | 6/1996 | Combs et al. | 606/167 |
| 6,056,735 A * | 5/2000 | Okada et al. | 606/1 |
| 6,193,653 B1 * | 2/2001 | Evans et al. | 600/210 |
| 6,217,599 B1 * | 4/2001 | McGuire | 606/184 |
| 6,936,069 B1 * | 8/2005 | Oladipo | 623/13.11 |

FOREIGN PATENT DOCUMENTS

| | | | |
|---|---|---|---|
| FR | 2824467 | * | 11/2002 |
| WO | WO9409708 | * | 5/1994 |
| WO | WO2006/119238 A2 | | 9/2006 |
| WO | PCT/US06/16720 | | 8/2007 |

OTHER PUBLICATIONS

Author Unknown, Graft Harvesting: Tendon Stripper, www.stryker.com, Stryker, Kalamazoo, USA.
Author Unknown, Graft Harvesting: Tendon Stripper, www.stryker.com, Stryker, Kalamazoo, USA. 2004 MBP.

* cited by examiner

*Primary Examiner*—Eduardo C. Robert
*Assistant Examiner*—Michael B. Priddy
(74) *Attorney, Agent, or Firm*—Taft Stettinius & Hollister LLP

(57) ABSTRACT

The invention includes a tendon stripper comprising: (a) a frame, including a cautery, that is adapted to separate surrounding tissue along a length of a tendon; (b) a handle mounted to the frame that is adapted to reposition the frame with respect to the tendon; and (c) an actuator in communication with the cautery and operative to activate the cautery, where activation of the cautery is adapted to sever the tendon. The invention also includes a method of stripping a tendon comprising: (a) exposing a tendon; (b) aligning a tendon stripper guide with respect to a first location to the tendon; (c) repositioning the tendon stripper guide along the tendon from the first location of the tendon to a second location of the tendon, where the act of repositioning of the tendon stripper guide is operative to separate surrounding tissue from the tendon between the first location and the second location; (d) activating a cautery to sever the tendon approximate the second location; and (e) cutting the tendon at a location other than the second location to provide a tendon segment.

8 Claims, 4 Drawing Sheets

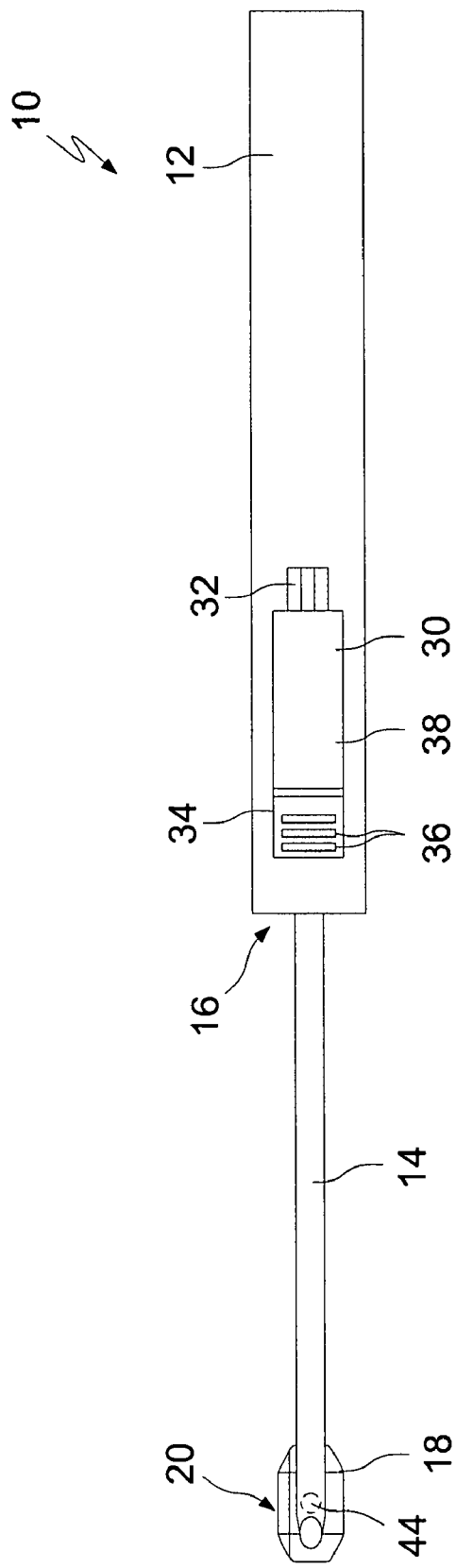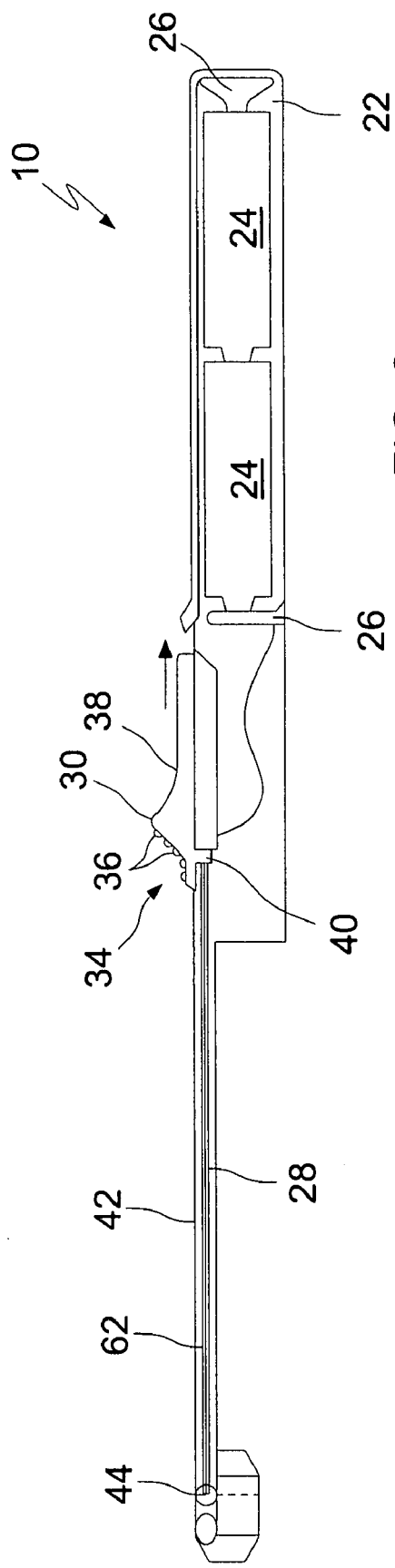

TENDON STRIPPER

RELATED ART

1. Field of the Invention

The present invention is directed to orthopedic surgical devices and associated methods of Minimally Invasive Surgery (MIS) and, more specifically, to tendon strippers and associated methods of harvesting tendons for use with MIS.

2. Brief Discussion of Related Art

The human body can frequently be impaired through dysfunction of an extremity commonly caused by loss of tendon or ligament function. Although repair of the ligament or tendon can be accomplished if the injury is recognized early, delayed treatment of these types of injuries or conditions may require a tendon transfer.

Tendon transfer utilizes the power and function of a normal tendon by surgically moving the tendon to another area of the body to substitute or supplement the function of an injured or diseased tendon. The surgical procedure involved with tendon transfer includes exposing both the diseased tendon and the normal tendon, as well as re-routing the origin or insertion of both tendons. A large incision is utilized with this technique to facilitate accurate placement of the transferred tendon. The tendon, once exposed, is transected under clear view of the surgeon and thereafter implanted in the desired location. Implantation may include anchoring the tendon to bone to mimic a new function, or include suturing and weaving the harvested tendon to the diseased tendon to supplement its strength.

The complications associated with conventional tendon transfer include the rather large surgical incision and resulting exposure. Scarring will frequently occur after surgery in a proportionate amount to the size and length of the incision and exposure. This scarring has been known to limit the function of the newly transferred tendon by adhering to the newly transferred tendon to its surrounding structure.

An exemplary tendon transfer may involve a torn tendon in the foot. The posterior tibial tendon is a critical tendon structure on the medial (inner border) side of the ankle. The ankle and foot will deviate in an outward direction as the posterior tibial posterior tibial tendon fails to function properly, thereby causing a progressive flatfoot deformity. If the posterior tibial tendon is near failure, the appropriate surgical intervention involves harvesting a neighboring tendon (flexor digitorum longus) and transferring the harvested tendon to the navicular bone to reestablish the normal function of the posterior tibial tendon. Harvesting the flexor digitorum longus tendon (as well as any other harvested tendon) generally requires extensive surgical dissection into the depths of the foot. The most common complication associated with this surgery is not the failure of the transferred tendon, but rather the pain and swelling associated with surgery around the critical veins and nerves in the foot. Thus, there is a need in the relevant art for surgical equipment and associated techniques for reducing the complications associated with tendon harvesting.

SUMMARY

The present invention is directed to orthopedic surgical devices and associated methods of Minimally Invasive Surgery (MIS) and, more specifically, to tendon strippers and associated methods of harvesting tendons for use with MIS.

It is a first aspect of the present invention to provide a tendon stripper comprising: (a) a frame, including a cautery, that is adapted to separate surrounding tissue along a length of a tendon; (b) a handle mounted to the frame that is adapted to reposition the frame with respect to the tendon; and (c) an actuator in communication with the cautery and operative to activate the cautery, where activation of the cautery is adapted to sever the tendon.

In a more detailed embodiment of the first aspect, the frame includes a distal guide adapted to at least partially circumscribe at least a portion of the tendon, where the distal guide is adapted to guide the frame along the length of the tendon. In yet another more detailed embodiment, the cautery includes an electrical cautery wire, the frame includes a housing along which the electrical cautery wire extends, the electrical cautery wire is longitudinally repositionable along a length of the housing, and the electrical cautery wire is mounted to the distal guide to at least partially circumscribe a portion of the tendon in a pre-severance position. In a further detailed embodiment, the electrical cautery wire is mounted to the actuator, and the actuator is operative to reposition the electrical cautery wire between the pre-severance position and a post-severance position, where the repositioning of the electrical cautery wire between the positions includes repositioning the electrical cautery wire along the length of the housing. In still a further detailed embodiment, the distal guide is arcuately shaped, and a distal end of the distal guide is tapered. In a more detailed embodiment, the distal guide includes a cylindrical portion, an aspect of the cylindrical portion is repositionable between an open position and a closed position, where the cylindrical portion circumscribes the tendon in the closed position and the cylindrical portion includes a latch operative to maintain the cylindrical portion in the closed position when engaged and is operative to allow the cylindrical portion to be positioned in the open position when disengaged.

In yet another more detailed embodiment of the first aspect, the electrical cautery wire is mounted to the cylindrical portion, the electrical cautery wire at least partially circumferentially lines a portion of an interior wall of the cylindrical portion in a U-shaped pre-severance position, and the electrical cautery wire is displaced from the U-shaped pre-severance position to a more taught post-severance position in order to sever the tendon. In still another more detailed embodiment, the handle includes a cavity adapted to house a portable power source, and the handle includes electrical leads adapted to be in electrical communication with the portable power source and the cautery. In a further detailed embodiment, the actuator is repositionably mounted to the handle, the cautery includes an electrical cautery wire, and the actuator is mounted to the electrical cautery wire so that movement of the actuator from a first position to a second position is operative to reposition the electrical cautery wire from a pre-severance position with respect to the tendon to a post-severance position with respect to the tendon.

It is a second aspect of the present invention to provide a method of stripping a tendon comprising: (a) exposing a tendon; (b) aligning a tendon stripper guide with respect to a first location to the tendon; (c) repositioning the tendon stripper guide along the tendon from the first location of the tendon to a second location of the tendon, where the act of repositioning of the tendon stripper guide is operative to separate surrounding tissue from the tendon between the first location and the second location; (d) activating a cautery to sever the tendon approximate the second location; and (e) cutting the tendon at a location other than the second location to provide a tendon segment.

In a more detailed embodiment of the second aspect, the act of aligning the tendon stripper guide includes opening the tendon stripper guide to allow insertion of the tendon and thereafter closing the tendon stripper guide to circumscribe the tendon to inhibit egress of the tendon in a radial direction. In yet another more detailed embodiment, the act of aligning the tendon stripper guide includes aligning the tendon stripper guide with respect to a tendon connected to bodily tissue at each end. In a further detailed embodiment, the act of aligning the tendon stripper guide includes providing a direct line of sight to the first location, and the act of repositioning the tendon stripper guide along the tendon includes discontinuing the direct line of sight prior to reaching the second location. In still a further detailed embodiment, the act of aligning the tendon stripper guide includes providing a direct line of sight to the first location, and the act of repositioning the tendon stripper guide along the tendon includes discontinuing the direct line of sight prior to reaching the second location. In a more detailed embodiment, the act of activating the cautery includes repositioning an actuator to provide electrical communication with a power source to energize the cautery.

In yet another more detailed embodiment of the second aspect, the cautery includes an electrical wire cautery, the electrical wire cautery is operatively coupled to the actuator, and the act of repositioning the actuator is operative to reposition the electrical wire cautery from a pre-severance position to a post-severance position. In still another more detailed embodiment, the cautery is mounted to an interior surface of the tendon stripper guide that at least partially circumscribes the tendon, and the tendon stripper guide is operative to inhibit destruction of the surrounding tissue when the cautery is activated.

It is a third aspect of the present invention to provide a method of stripping a tendon comprising: (a) exposing a tendon; (b) aligning a tendon stripper guide with respect to a first location to the tendon; (c) repositioning the tendon stripper guide along the tendon from the first location of the tendon to a second location of the tendon, where the act of repositioning of the tendon stripper guide is operative to separate surrounding tissue from the tendon between the first location and the second location; (d) tensioning a cutting wire to sever the tendon approximate the second location; and (e) cutting the tendon at a location other than the second location to provide a tendon segment.

The aforementioned aspects should not be considered a completely inclusive summary of the present invention. Reference is had to the Detailed Description for a more accurate and inclusive understanding of the invention.

BRIEF DESCRIPTION OF THE DRAWINGS

FIG. 1 is an overhead view of a first exemplary embodiment of the present invention;

FIG. 2 is a left side perspective view of the first exemplary embodiment of FIG. 1, shown with a cut-away view of the exemplary handle;

DETAILED DESCRIPTION

The exemplary embodiments of the present invention are described and illustrated below to encompass orthopedic surgical devices and associated techniques that are applicable in areas such as, without limitation, tendon harvesting and Minimally Invasive Surgery (MIS). Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 3:
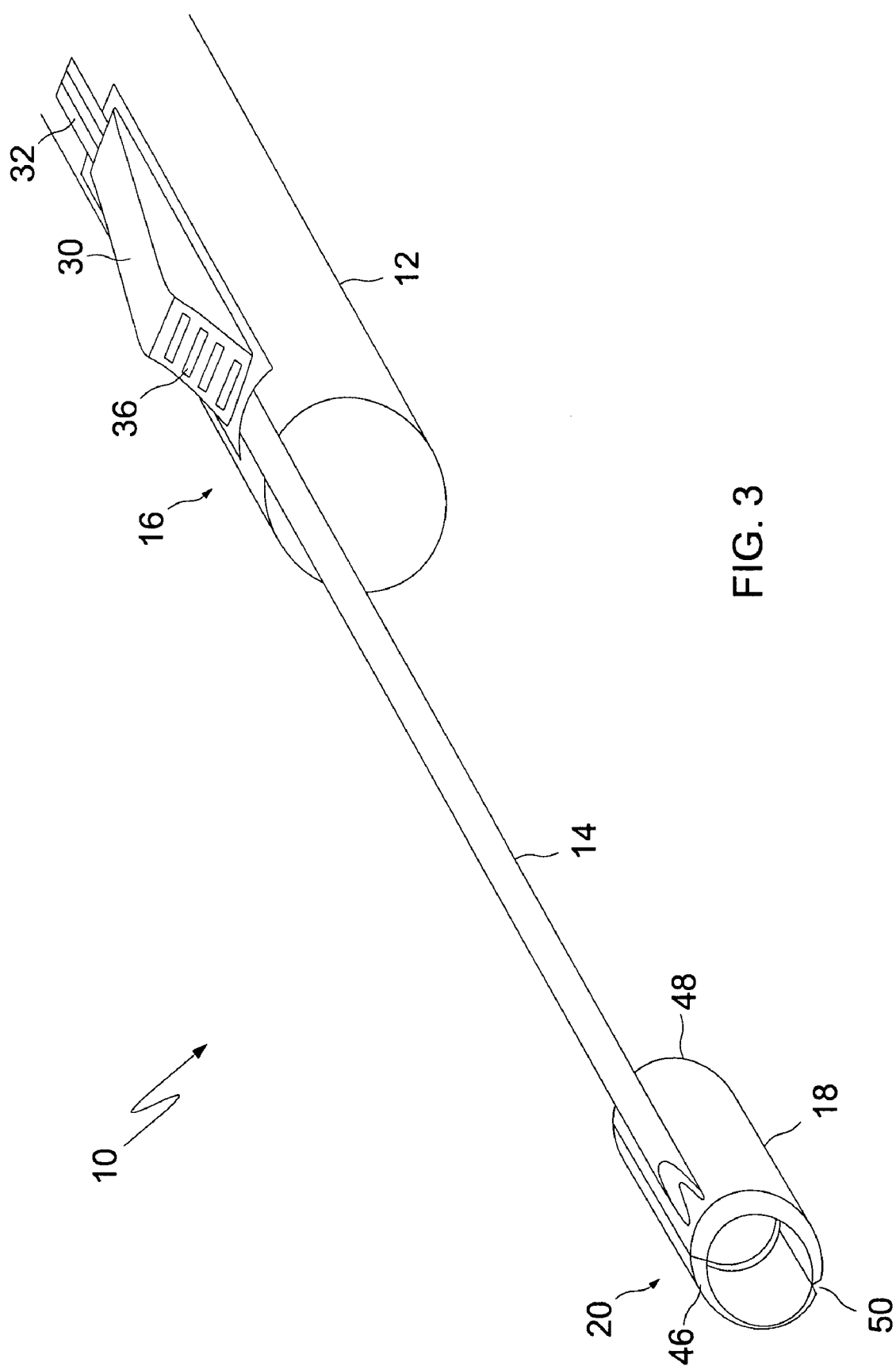
FIG. 3 is a frontal elevated perspective view of the first exemplary embodiment of FIG. 1.

Referencing FIGS. 1-3, a first exemplary tendon stripper 10 includes a handle 12 mounted to a semiflexible plastic connecting rod 14 at a proximal end 16. The connecting rod 14 extends outward from the handle 12 and is mounted to a plastic barrel 18 at a distal end 20. The handle 12 includes a cavity 22 adapted to house a portable power source 24 such as, without limitation, batteries. Electrical leads 26 housed within the cavity 22 provide electrical communication between one of a set of contact plates (not shown) and the batteries 24, while a second contact plate is in electrical communication with an electrically powered cautery 28. For purposes of explanation only, the electrically powered cautery 28 of the first exemplary embodiment is described as an electrical monofilament wire cautery. Those of ordinary skill will readily understand that other cautery devices may be used in lieu of or in addition to the electrical monofilament wire cautery 28 such as, without limitation, monopolar/bipolar cautery, radiofrequency probe, optical filament, or laser energy.

In exemplary form, the handle 12 of the stripper 10 is intended to be seated within the palm of the user's hand, with the user's finger wrapping around the handle 12 and the user's thumb facing the barrel 18. An actuator 30 repositionably mounted to the handle 12 is intended to be engaged by a user's thumb in order to reposition the actuator and activate the electrical wire cautery 28. The actuator 30 rides within a channel 32 formed within the surface of the handle 12 that provides linear travel forward and backward (as shown by the arrow of FIG. 2). A forward depression 34 within the actuator 30 includes a plurality of horizontal plateaus 36 that are adapted provide a gripping surface for user's thumb to engage while moving the actuator backward. In addition, the actuator 30 includes a second, reward depression 38 adapted to receive a user's thumb when moving the actuator 30 forward.

The underside of the actuator 30 includes a corresponding set of contact plates (not shown) that provide electrical communication between the batteries 24 and the electrical wire cautery 28 after the actuator is moved rearward beyond a predetermined point. Those of ordinary skill will realize that the precise point at which the contact plates close the circuit to provide electric current to the cautery 28 is within the purview of one of ordinary skill and may be changed without departing from the scope and spirit of the present invention. Likewise, it is within the scope of the invention to provide a separate actuator (other than the actuator 30 mounted to the electrical wire cautery 28) that is responsible for establishing electrical communication between the cautery 28 and batteries 24.

A frontal aspect 40 of the actuator 30 is coupled to the electrical wire cautery 28, which extends through a cylindrical conduit 42 extending substantially the entire length of the connecting rod 14. The electrical wire cautery 28 exits the distal end of the connecting rod 14 through a hole 44 connecting the interior of the conduit 42 with the interior of the barrel 18.

Figure 4:
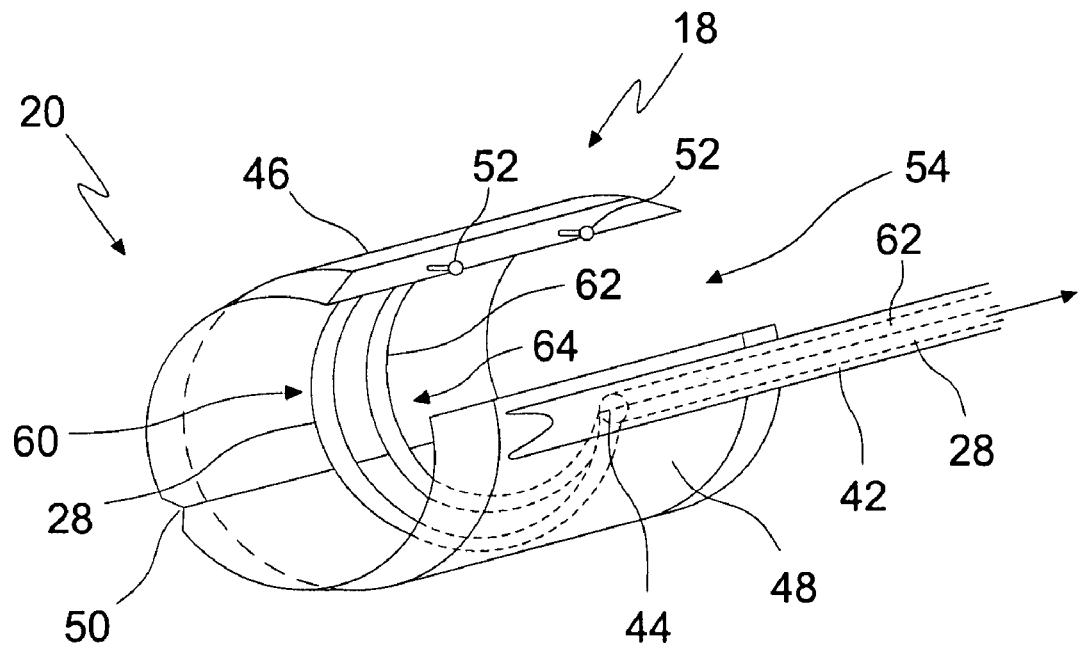
FIG. 4 is an elevated perspective view of the exemplary barrel of the first exemplary embodiment of FIG. 1, shown in the open position.

Referring to FIG. 4, the barrel 18 includes a first semiannular section 46 that is repositionable with respect to a second semiannular section 48 by way of a hinge 50 and catch 52. The hinge 50 may be a living hinge or mechanical hinge operative to allow an opening 54 between the sections 46, 48 to accommodate a linear section of a tendon to be lowered into the interior of the barrel 18. It is to be understood that the hinged barrel 18 of the first exemplary tendon stripper 10 accommodates tendons that are either detached from bodily tissue at one or both ends, as well as tendons attached to bodily tissue at opposing ends. Exemplary manually operative catches or fasteners 52 may be snap-fit or any other type of catch/fastener that provides for selective opening and closing of the sections 46, 48. It is also within the scope of the invention that the catch be automatically operated. In the closed position, the sections 46, 48 provide a cylindrical barrel 18 that includes a circular cross-section. Nevertheless, it is to be understood that the dimensions and contours of the barrel 18 are exemplary in nature and may be reconfigured to include, without limitation, rectangular cross-sections and oblong circular cross-sections. As will be discussed in more detail below, the distal end 20 of each of the sections 46, 48 and the distal end 20 of the connecting rod 14 are beveled to decrease the resistance to longitudinal movement of the barrel 18 in the proximal direction to strip the tissue surrounding the tendon as the barrel 18 progresses along the length of the tendon.

Figure 5:
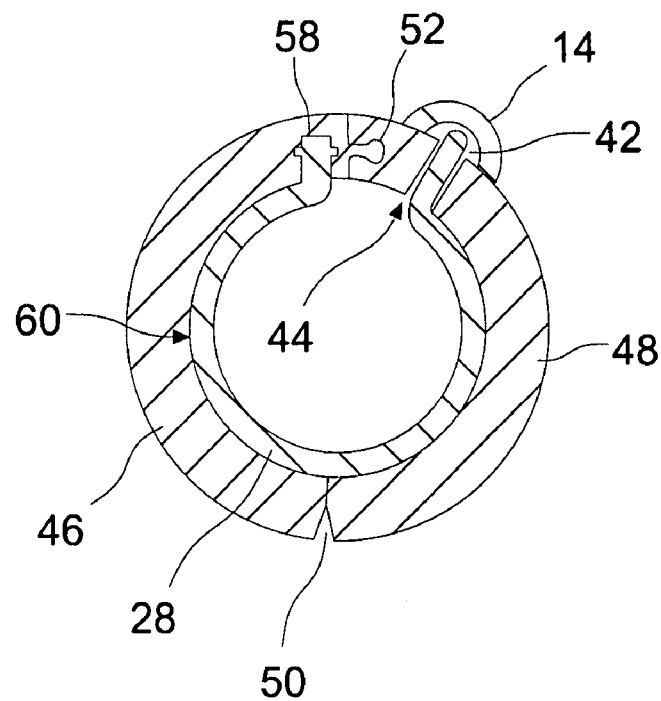
FIG. 5 is a cross-sectional view of the exemplary barrel of FIG. 4 in the closed position, where the cautery wire is shown in the pre-severance position.
Figure 6:
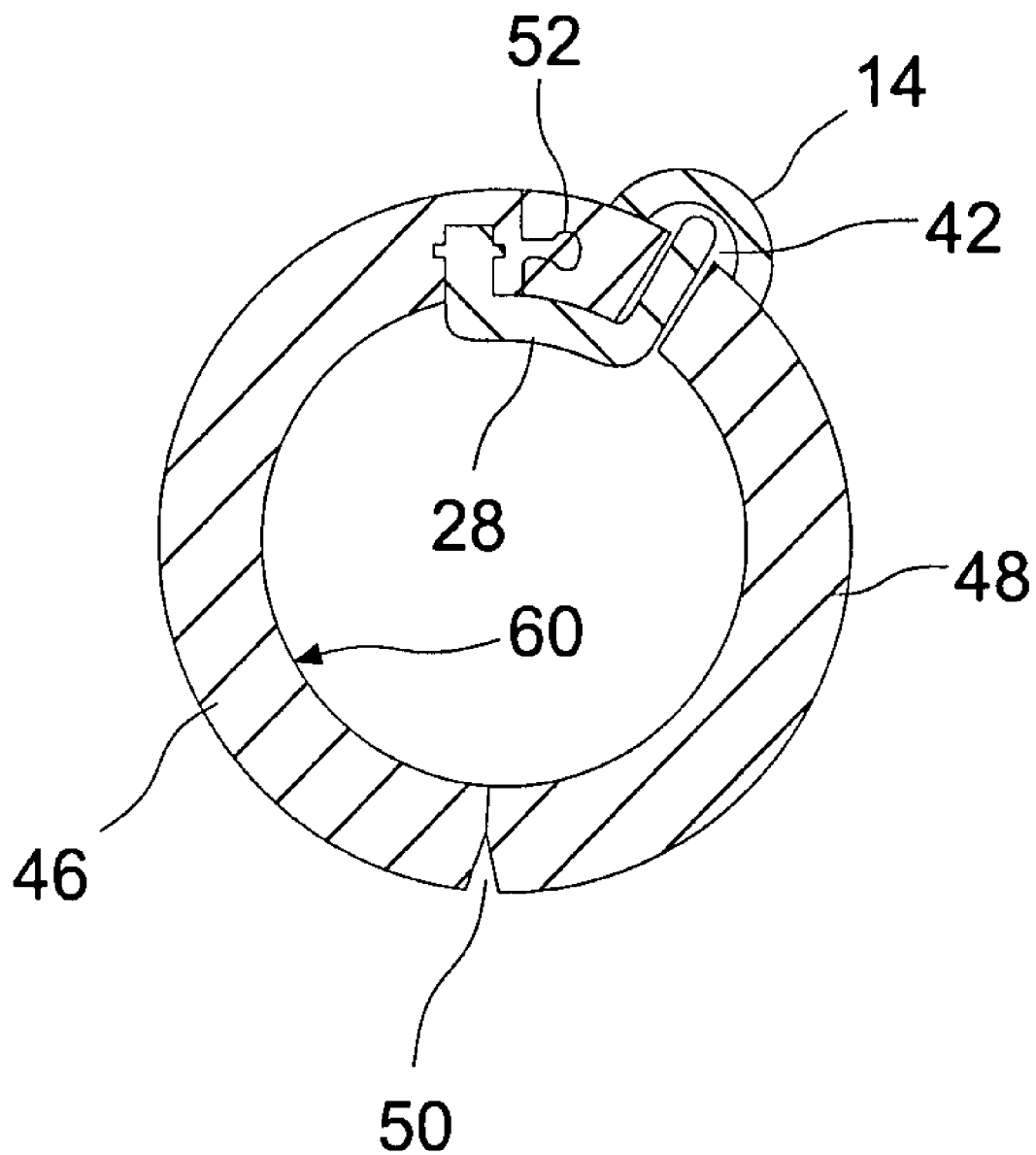
FIG. 6 is a cross-sectional view of the exemplary barrel of FIG. 4 in the closed position, where the cautery wire is shown in the post-severance position.

Referring to FIGS. 4-6, the electrical wire cautery 28 is anchored within a cavern 58 of the first semiannular section 46. The electrical wire cautery 28 extending beyond the cavern 58 is seated within a circumferential recess 60 of the interior of the barrel 18 (formed by the two semiannular interior surfaces of the sections 46, 48) to circumferentially line the interior until reaching the hole 44 leading out of the barrel 18 in the "slacked position." This slacked position (see FIGS. 3 and 4) corresponds with the position of the actuator 30 in the most forward position or in pre-severance position where the electrical wire cautery 28 accommodates the shape of the tendon. In contrast, when the actuator 30 is repositioned rearward (see FIG. 2), the length of the electrical wire cautery 28 within the barrel 18 is substantially decreased resulting in a "taught position" or post-severance position (see FIG. 6). A return wire 62, in electrical communication with anchored aspect of the wire cautery 28, runs parallel to the cautery wire in a separate recess 64 within the interior of the barrel 18. The return wire 62 exits the barrel 18 through the hole 44 and extends through the cylindrical conduit 42 of the connecting rod 14 until reaching the interior of the handle and into electrical communication with one of the electrical contact plates. As discussed above, when the actuator 30 is repositioned rearward to an extent to allow for contact between the electrical contact plates, the electrical circuit is closed and the electrical wire cautery 28 is energized resulting in the wire becoming heated to a sufficient degree to burn through the tendon within the barrel 18.

The stripper 10 is manufactured in variable sizes to precisely allow various diameters and lengths of tendons to be harvested. By matching the diameter of the barrel 18 to the prospective tendon to be harvested, the surrounding soft tissue is protected from inadvertent entry. Exemplary measurements for components of the tendon stripper 10 include an overall length of 40 cm. The handle 12 includes a length of 15 cm and a diameter of 2 mm diameter. The handle 12 may be fabricated from plastic. The electrical wire cautery 28 is commercially available from Malin Company, Inc., 5400 Smith Road, Cleveland, Ohio 44142 and may be tailored to match the preferred length of the rod 14 and circumference of the barrel 18. The connecting rod 14 is flexible and commercially available from The MedTech Group, Inc., 6 Century Road, South Plainfield, N.J. 07080. The barrel 18 is fabricated from a surgically acceptable plastic and includes a length of approximately 1.5 cm and a diameter ranging between approximately 4.0 mm. to about 9.0 mm.

The electrical wire cautery 28 of the present invention may comprise at least two aspects. A first aspect of the wire cautery 28, positioned within the barrel 18 as shown in FIGS. 4 and 5, may be comprised of a high resistance filament, whereas a second aspect comprising the remainder of the wire cautery 28 may be comprised of a low resistance wire. The lengths of the first and second aspects of the electrical wire cautery 28 are well within the purview of one of ordinary skill.

The exemplary tendon stripper 10 may be utilized for accurate and atraumatic harvesting of a tendon failing to include a detached free end. A small 3 cm incision is made to expose a subcutaneous portion of a tendon. The catch 52 is released to allow the semiannular sections 46, 48 of the barrel 18 to be separated via movement of the hinge 50 to create the opening 54 through which the viewed tendon is longitudinally repositioned to pass through and lie on the interior of the barrel 18. After the tendon is located in the interior of the barrel 18, the sections 46, 48 are brought together to close the opening 54 and the catch 52 is secured.

The barrel 18 is advanced within the tissue plane of the tendon until reaching a predetermined location, while concurrently avoiding exposure of companion neurovascular structures. Movement of the barrel 18 along the tendon is operative to separate the tendon from surrounding bodily tissue. Once the barrel 18 is advanced to a predetermined location along of the tendon, the actuator 30 is repositioned rearward away from the barrel 18 to provide contact between the metal plates to close the circuit and energize the electrical wire cautery 28 positioned underneath of the tendon. As actuator 30 is moved further away from the barrel 18, portions of the electrical wire cautery 28 are drawn out of the barrel 18 through the hole 44, thereby reducing the length of the electrical wire cautery 28 remaining within the barrel 18. The tendon in the path of the moving electrical wire cautery 28, while energized, is cauterized. Eventually, enough of the electrical wire cautery 28 is withdrawn from the barrel 18 to arrive at the taught position shown in FIG. 6. At this point, any tendon within the barrel 18 is completely severed by the action of the electrical wire cautery 28. The tendon is pulled away from the barrel 18 and delivered to the incision. The actuator 22 is pushed to an off position and the stripper 10 is withdrawn.

The exemplary stripper 10 is advantageous in both arthroscopy and MIS applications to minimally disrupt surround soft tissue structures. The body responds to less injury and heals faster as the incision and wound is smaller by using a stripper 10 that does not require line of sight prior to cauterizing the tendon, nor requires that one end of the tendon be free prior to cauterization. Moreover, the surrounding tissue is protected from the heat of the cauterization by the barrel 18 of the tendon stripper 10.

It is also within the scope of the present invention to exchange the cautery 28 for a razor wire. In this manner, the actuator might be rearwardly repositioned to withdraw a portion of the razor wire from the barrel in a manner that would be operative to sever the tendon. It is also within the scope of the invention to provide a delivery system for optical cable to deliver laser energy or to use the barrel to deliver a probe for radiofrequency energy or monopolar/bipolar electrocautery.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of stripping a tendon comprising:

exposing a tendon;

aligning a tendon stripper guide with respect to a first location to the tendon so at least a portion of the tendon extends through the guide;

repositioning the tendon stripper guide along the tendon from the first location of the tendon to a second location of the tendon, where the act of repositioning of the tendon stripper guide is operative to separate surrounding tissue from the tendon between the first location and the second location;

tensioning a cutting wire with respect to the guide to sever the tendon approximate the second location while the tendon is extending through the guide; and cutting the tendon at a location other than the second location to provide a tendon segment.

2. A method of stringing a tendon comprising:

exposing a tendon:

aligning a tendon stripper guide with respect to a first location of the tendon;

repositioning the tendon stripper guide along the tendon from the first location of the tendon to a second location of the tendon, where the act of repositioning of the tendon stripper guide is operative to separate surrounding tissue from at least a portion of the tendon between the first location and the second location;

activating a cautery to sever at least the portion of the tendon approximate the second location; and cutting at least a portion of the tendon at a location other than the second location to provide a tendon segment, wherein:

the act of activating the cautery includes repositioning an actuator provide electrical communication with a power source to energize the cautery;

the cautery includes an electrical wire cautery;

the electrical wire cautery is operatively coupled to the actuator; and the act of repositioning the actuator is operative to reposition the electrical wire cautery from a pre-severance position to a post-severance position.

3. A method of stripping a tendon comprising:

exposing a tendon;

aligning a tendon stripper guide with respect to a first location of the tendon;

repositioning the tendon stripper guide along the tendon from the first location of the tendon to a second location of the tendon, where the act of repositioning of the tendon stripper guide is operative to separate surrounding tissue from at least a portion of the tendon between the first location and the second location;

activating a cautery to sever at least the portion of the tendon approximate the second location; and cutting at least a portion of the tendon at a location other than the second location to provide a tendon segment, wherein:

the cautery is mounted to an interior surface of the tendon stripper guide that at least partially circumscribes at least the portion of the tendon; and the tendon stripper guide is operative to inhibit destruction of the surrounding tissue when the cautery is activated.

4. A method of stripping a tendon comprising:

exposing a tendon;

aligning a tendon stripper barrel around at least a portion of the tendon at a first location along a length of the tendon;

repositioning the tendon stripper barrel along the portion of the tendon from the first location of the tendon to a second location along the length of the tendon, where the act of repositioning of die tendon stripper barrel is operative to separate surrounding tissue from the portion of the tendon between the first location and the second location;

tensioning a cutting wire to sever the tendon approximate the second location; and cutting the tendon at a location other than the second location to provide a tendon segment.

5. The method of claim 4, wherein:

the act of aligning the tendon stripper barrel around at least the portion of the tendon includes enclosing a housing of the teddon stripper barrel around at least the portion of the tendon prior to repositioning the tendon stripper barrel along the tendon.

6. The method of claim 5, wherein:

the tendon stripper barrel includes a first housing member pivotally repositionable between a fastened position and a free position to provide selective access to an interior of the tendon stripper barrel; and the act of enclosing the housing of the tendon stripper barrel includes pivoting the first housing member from the free position to the fastened position.

7. A method of stripping a tendon comprising:

exposing a tendon;

repositioning a tendon stripper alone the tendon from the first location of the tendon to a second location of the tendon, where the act of repositioning of the tendon stripper is operative to separate surrounding tissue from at least the portion of the tendon between the first location and the second location;

activating a cautery to sever at least the nortion of the tendon approximate the second location;

cutting at least a portion of the tendon at a location other than the second location to provide a tendon segment; and closing a housing of the tendon stripper around at least the portion of the tendon prior to repositioning the tendon stripper along the tendon.

8. The method of claim 7, wherein:

the tendon stripper includes a first housing member pivotally repositionable between a fastened position and a free position to provide selective access to an interior of the tendon stripper; and the act of enclosing the housing of the tendon stripper includes pivoting the first housing member from the free position to the fastened position.

* * * * *